United States Patent [19]

Burgoyne, Jr. et al.

[11] Patent Number: 5,001,263
[45] Date of Patent: Mar. 19, 1991

[54] FORMATION OF ORTHO-ALKYLATED AROMATIC AMINES FROM N-ALKYLATED AROMATIC AMINES

[75] Inventors: William F. Burgoyne, Jr., Allentown; Dale D. Dixon, Kutztown, both of Pa.

[73] Assignee: Air Products and Chemicals, Inc., Allentown, Pa.

[21] Appl. No.: 767,945

[22] Filed: Aug. 21, 1985

[51] Int. Cl.$^5$ ............................................. C07C 209/68
[52] U.S. Cl. ................................................... 564/409
[58] Field of Search ........................................ 564/409

[56] References Cited

U.S. PATENT DOCUMENTS

| | | | |
|---|---|---|---|
| 2,115,884 | 5/1938 | Schöllkopf | 260/168 |
| 2,762,845 | 9/1956 | Stroh et al. | 260/578 |
| 2,923,745 | 2/1960 | Buls et al. | 260/624 |
| 3,275,690 | 9/1966 | Stroh et al. | 260/576 |
| 3,649,693 | 3/1972 | Napolitano | 260/578 |
| 3,701,811 | 10/1972 | Nicklin | 260/621 R |
| 3,733,365 | 5/1973 | Yeakey et al. | 260/624 C |
| 3,923,892 | 12/1975 | Klopfer | 260/578 |
| 4,351,958 | 9/1982 | Takahata | 564/409 |
| 4,446,329 | 5/1984 | Waller | 585/458 |

FOREIGN PATENT DOCUMENTS

| | | |
|---|---|---|
| 1051271 | 2/1959 | Fed. Rep. of Germany . |
| 38-4569 | 4/1963 | Japan . |
| 59-167545 | 9/1984 | Japan . |
| 421791 | 12/1934 | United Kingdom . |
| 846226 | 8/1960 | United Kingdom . |

OTHER PUBLICATIONS

Chemical Abstracts, (43), 4644(f), (1949), Lavrovskii et al.
Chemical Abstracts (94), 163245p, (1981), Zarubina et al.
Chemical Abstracts, (83), 134815s, (1975), Borukhova et al.
Hart-Kosak, J. Org. Chem., 27, 116 (1962).
Hart-Kosak, J. Org. Chem., 22, 1752 (1957).
Reilly and Hickenbottom, J. Chem., Soc., 117, 103, (1920).

Primary Examiner—Charles F. Warren
Attorney, Agent, or Firm—Russell L. Brewer; James C. Simmons; William F. Marsh

[57] ABSTRACT

This invention relates to a process for producing ring alkylated aromatic amines where the alkyl substituent is ortho to the amino group by reacting an N-alkylated aromatic amine with a $C_{2-10}$ olefin in the presence of a solid phase acidic catalyst, e.g., silica-alumina or a zeolite. High conversion and selectivity is achieved by maintaining a mole ratio of olefin to amine of from about 1-10:1 and an operating pressure of at least 50 psig.

14 Claims, No Drawings

FORMATION OF ORTHO-ALKYLATED AROMATIC AMINES FROM N-ALKYLATED AROMATIC AMINES

TECHNICAL FIELD

This invention pertains to a process for the conversion of N-alkylated aromatic amines to the ortho-alkylated counterpart.

BACKGROUND OF THE INVENTION

Processes for alkylating a variety of aromatic compounds by contacting such compounds with a hydrocarbon radical providing source such as an olefin or alcohol with an alkylatable aromatic compound are widely known. Typically, alkylatable aromatic compounds have included mononuclear aromatic compounds themselves or aromatic compounds containing polar substituents such as a hydroxyl, an amino, an alkoxy, a halogen group and so forth. The catalysts utilized in the alkylation reactions have been acidic; e.g., Lewis acids and used as Friedel-Crafts catalyst systems.

To facilitate an understanding of the scope of alkylation of aromatic compounds including the types of aromatic compounds which are alkylatable and the catalyst systems, reference is made to the following patents:

U.S. Pat. No. 2,115,884 discloses the alkylation of aromatic hydrocarbons such as benzene and napthalene, as well as their halogen, nitro, carboxylic acid, and amine derivatives. The alkylation is effected by contacting the aromatic compound with an olefin while using a hydrated silica or bleaching earth as a catalyst. Temperatures of about 140°–260° C. are used.

U.S. Pat. Nos. 3,733,365; 2,923,745; and 3,701,811 disclose the alkylation of hydroxy aromatics, e.g. phenol, by contacting the aromatic compound with an olefin or alcohol. The catalyst systems utilized in these alkylation processes include polymeric aluminum alcoholates, active alumina activated with an aluminum alcoholate, aluminum halides and metal oxides such as cerium oxide or uranium oxide disposed upon inert carriers such as gamma-alumina, silicon carbide, silica and natural clays, molecular sieves and alumino-silicates.

The ring-alkylation of aromatic amines has generated considerable interest because the aromatic monoamines are valuable intermediates in the manufacture of herbicides, dyestuffs, auxiliaries for rubber and plastics and for textiles. Alkylated diamines have many of the same uses that the mono aromatic amines have, but they may also be used as cross linkers for producing a variety of polyurethanes. The alkylated aromatic amines, particularly toluenediamine, when alkylated have a lower reactivity than the parent aromatic amine and this permits manufacturers to form a variety of molded products in a way that could not be formed earlier. Reaction injection molding (RIM) is one of these processes which lends itself to the use of ring-alkylated aromatic diamines as chain extenders for polyurethanes.

Early processes for the ring-alkylation of aromatic amines resulted from the reaction of aniline hydrochloride with alcohols. Similar results were obtained when an N-alkylanilinium halide was heated and caused to rearrange to the ring alkylated product. This work was done by Hofmann and Martius.

Reilly and Hickenbottom, published in a series of articles, one appearing in J. Chem. Soc., 117, 103, (1920) that nuclear alkylation of amines could be effected by heating an N-alkylaniline with a Lewis acid, such as, zinc chloride.

U.S. Pat. Nos. 3,649,693; and 3,923,892 disclose the preparation of ring-alkylated aromatic amines where the alkyl group is ortho to the amine. The U.S. Pat. No. '693 discloses ring alkylation by reacting an aromatic amine with an olefin in the presence of aluminum anilide. The U.S. Pat. No. '892 shows the alkylation in the presence of an alkyl aluminum halide such as diethyl aluminum chloride. The U.S. Pat. No. '892 shows the alkylation reaction in the presence of aluminum anilide.

Stroh et al. in U.S. Pat. No. 3,275,690; 2,762,845; West German AS No. 1,051,271 and Japanese No. 38-4569 disclose various processes for the manufacture of alkylated aromatic amines by effecting reaction between an aromatic amine and an olefin. Representative aromatic amines for alkylation include primary amines, such as, aniline, toluidines, xylidines; secondary amines such as diphenylamine and diamines such as m-phenylenediamine and various toluenediamine isomers. In the U.S. Pat. No. '690, various Friedel-Crafts catalysts such as aluminum chloride, zinc chloride, boron fluoride and other halogen compounds are combined with aluminum to effect the catalytic reaction. In the U.S. Pat. No. '845, aluminum powder is used as a component of the catalyst system. The West German No. '271 uses various bleaching earths and montmorillonite as the catalyst.

Most of the above processes utilize homogeneous catalysis. However, the heterogeneous catalysis of the alkylation of aromatic amines is shown in U.S. Pat. No. 2,115,884; British patent No. 846,226; U.S. Pat. Nos. 4,351,958 and 4,446,329. The U.S. Pat. No. '884 discloses the ring alkylation of aromatic hydrocarbons using activated hydrosilicates and hydrated silicic acids, commonly referred to as bleaching earth. The U.S. Pat. No. '958 discloses the use of iron oxide as a catalyst for such alkylation and the U.S. Pat. No. '329 discloses the use of a metal cation salt of a perfluorosulfonic acid polymer, the polymer typically being sold under the trademark Nafion.

Japanese Patent No. 59-167545 discloses the reaction of N-isopropyl-3-methylaniline in the presence of propylene and a Friedel-Crafts catalyst. The 3-methyl-4-isopropylaniline derivative is produced.

One of the problems associated with the ring-alkylation of aromatic amines with an olefin, even though such processes are alleged to be effective for ortho-alkylation or para-alkylation, is that a large amount of N-alkylated aromatic amine is produced. The N-alkylated product formed in amounts from 2–45% by weight of reactant must be converted to a ring-alkylated product in order for the overall process to have any industrial success. A second problem associated with the ring-alkylation of N-alkylated aromatic amines is that the N-alkylated aromatic amine readily rearranges in the presence of the catalyst to the para-isomer. Under alkylation conditions, particularly at high conversions, e.g., greater than 20%, the amount of para-isomer formed is quite high in relation to the amount of ortho-isomer. Typically, the ortho-para isomer ratio is less than 3:1 and generally less than 1:1. Some other problems described herein regarding the synthesis of ortho-alkylated amine products and those problems associated with the production of N-alkylated aromatic amines are well-illustrated in U.S. Pat. No.

4,351,958, Column 1, lines 32-67, and Column 2, lines 1-34.

SUMMARY OF THE INVENTION

This invention pertains to a process for enhancing the conversion of N-alkylated aromatic amines to a ring-alkylated amine where the alkyl group is ortho to the amine. Both high selectivity to the ortho-isomer as opposed to the para-isomer and high conversion to the ring-alkylated product is achieved. More particularly, the process for producing a reaction product having a high ortho to para isomer ratio of ring-alkylated product e.g. greater than 3:1 at greater than 20% conversion is effected by reacting a feed composition capable of alkylation in the ortho and para positions represented by the formula:

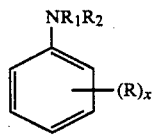

where R is hydrogen or $C_1$ to $C_{10}$, X is 0, 1 or 2, $R_1$ is $C_2$ to $C_{10}$ alkyl and $R_2$ is hydrogen or $C_1$ to $C_{10}$ alkyl. The reaction is carried out by contacting the N-alkylated reactant with an olefin over a solid phase, acid catalyst, and maintaining an olefin to N-alkylate molar ratio of at least 1:1. The temperature employed in the reaction is that temperature which is sufficient to effect conversion of the N-alkylated reactant to ring alkylated product, but insufficient to effect substantial decomposition of the ortho-alkylated product as it is produced. During such reaction the pressure sufficient to aid in rearrangement is greater than 50 psig but not in excess of 3000 psig.

There are many advantages associated with this invention, and these include:

an ability to selectively generate ring-alkylated aromatic amines where the alkyl group is ortho to the amine as opposed to para to the amine; e.g., ratios greater than 3:1;

an ability to effect the catalytic reaction in the presence of a heterogeneous catalytic system which provides a mechanism for easy separation of the catalyst from the reaction medium and a mechanism for continuous operation;

an ability to convert byproduct N-alkylated aromatic amine to valuable ring-alkylated product at high conversion; and an ability to achieve ring-alkylation of N-alkyl aromatic amines at modest pressures, thus reducing capital costs with respect to equipment, while at the same time obtaining high reaction rates and conversions.

DETAILED DESCRIPTION OF THE INVENTION

The feedstock suited for practicing this invention contains an N-alkylated aromatic amine such as an N-monoalkyl aromatic amine or an N,N-dialkyl aromatic amine. Such N-alkylated aromatic amines typically result as a byproduct from the alkylation of aromatic amines such as aniline and toluidine. Such N-alkylated reactant is represented by the formula:

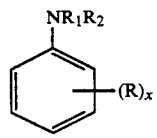

where R is hydrogen or $C_1$ to $C_{10}$, X is 0, 1 or 2, $R_1$ is $C_2$-$C_{10}$ alkyl and $R_2$ is hydrogen or $C_1$ to $C_{10}$ alkyl. Specific examples of N-alkylated reactants include N-ethylaniline, N-isopropylaniline, N,N-diethylaniline, N,N-diisopropylaniline, N-ethyl-2-toluidine, N-ethyl-2,4-xylidine, N-tert-butyl-2,4-xylidine, N-tert-butylaniline and the like. These amines may also be substituted with substituents inert to the alkylation reactions; e.g. halogen atoms; e.g., chloro and bromo; ester groups etc. Preferably R' is hydrogen or $C_{1-4}$.

The alkylation of the N-alkylated reactant is achieved by reacting a $C_2$-$C_{10}$, preferably $C_{2-6}$, unsaturated olefin with the alkylatable aromatic amine reactant with the olefin to amine molar ratio being at least 1:1 and generally 2-10:1. Although other hydrocarbons have been utilized in the alkylation of aromatic hydrocarbons; e.g., alcohols, many of these alkylating agents undergo condensation with the N-alkylated reactant producing water which tends to destroy activity and alter the reactivity and selectivity to the ortho-isomer. Examples of olefins suited for practicing the invention include ethylene, propylene, isobutylene, pentene, and cyclohexene.

The catalysts used in the reaction of the present invention are those which are solid phase and which have sufficient catalytic activity to effect ring-alkylation. These catalysts must be acidic, although the degree of acidity of the catalysts may vary from one catalyst system to another. The only criteria is that the catalyst selected is sufficiently reactive for the aromatic compound and olefin selected to effect rearrangement. Examples of solid phase catalyst systems which are sufficiently active for effecting ring-alkylation of the N-alkylated aromatic amine include acidic zeolites, primarily those zeolites which have a pore size from 6 to 15 Angstroms and which have been ion exchanged with hydrogen or an acidic metal, e.g., lanthanum or other rare earth metal. Examples of such zeolite catalysts include mordenite, the Y and X faujasites, erionite, clinoptilolite the ZSM family and so forth. The zeolite also can be altered by the technique of "dealumination"; i.e., a technique where the alumina content is decreased in the zeolite. Dealumination, i.e., the removal of alumina from a zeolite structure has the effect of increasing the acidity of the catalyst system and also one of enlarging the pore size of the zeolite. Dealumination can be effected by acid treatment, chelation, dehydration, or steam treatment of the zeolite. A Si to Al ratio of a dealuminated zeolite typically will range from about 5 to 25:1.

These zeolites can be exchanged with various ions, preferably hydrogen or with a rare earth metal ion such as lanthanum, praeseodymium, and the like. The use of various ions in the structure will alter the acidity of the catalyst and therefore the reactivity in the alkylation reaction. Alkali metal ions create a zeolite catalyst which is less acidic and high temperatures may be required to effect alkylation. These high temperatures may influence transalkylation and thus formation of the para isomer. It should be recognized by those familiar with the utilization of zeolites in the alkylation of aromatic compounds that the pore size will vary between zeolites, and appropriately sized zeolites must be used to accommodate the synthesis of the higher molecular weight ring-alkylated aromatic amines and the multi-alkylated aromatic amine compounds. In most cases for alkylation, the pore size of the zeolite should be in excess of 7 Angstroms.

Other heterogeneous solid phase catalyst systems include montmorillonite, gamma-alumina, silica-alumina, and the like. Gamma-alumina is particularly effective for achieving high selectivity to ortho alkylated product.

The alkylation of N-alkylated aromatic amine is carried out at a temperature ranging from about 50° to 375° C. and typically at a pressure from about 50 to 3000 psig, typically 200-2000 and preferably from about 500-1000 psig. The temperature is controlled within this range at a temperature which is sufficiently high for the reactants to be reactive in the presence of the catalyst. Temperature control is an important variable in producing a reaction product which has a high ortho to para molar ratio and with a high conversion of N-alkylate to ring-alkylated product.

The alkylation of N-alkyl aromatic amine occurs with increasing ease as substitution of the double bond increases. For example, isobutylene will react faster than propylene and propylene will react faster than ethylene. Thus, an N-ethyl alkylated product will be stable at a higher temperature in the reaction zone than the N-isopropyl radical or the N-t-butyl radical under a given set of reaction conditions. Depending upon the acidity of the catalyst and activity of the amine, ethylene alkylation of N-ethylated aromatic amines may be accomplished at a temperature from about 200°-425° C., while the propylene alkylation may be effected within a range of 100°-375° C. and the isobutylene alkylation of N-t-butyl aromatic amine may be effected at a lower temperature; e.g., from 50°-250° C.

Temperature is an important parameter in achieving high conversion of the N-alkylated reactant to ring-alkylated product. However, as the temperature is increased for a given set of reaction conditions, there is the danger of effecting rereaction of the ortho-ring-alkylated product to form the para isomer or dealkylation of the ring-alkylated product. Typically, for ethylene alkylation of N-ethyl aromatic amine, the temperature should not exceed 425° C. For propylene alkylation, the temperature should not exceed 375° C. and for isobutylene alkylation, the temperature should not exceed 250° C.

Reaction time is also an important factor in achieving high selectivity to the ortho-alkylated product at high conversion. Broadly, the reaction time can be expressed as a liquid hourly space velocity of feed components to the reactor and such expression will generate an LHSV of from 0.05 to 4 hours$^{-1}$ and usually from 0.1 to 1 hr$^{-1}$. If one is operating at relatively high temperatures for the alkylation reaction, the LHSV should be increased somewhat as longer reaction times permit increased formation of the para isomer. In those cases where high temperatures and long residence times are used, the rate of formation of ortho-isomer is less than the rate of dealkylation and transalkylation to para-isomer and thus lower ortho to para ratios are produced. The control of temperature, olefin ratio and pressure tend to suppress the rate of dealkylation and transalkylation and enhance the conditions for ortho alkylation.

By utilizing the above catalysts and exercising control of the reaction parameters, ortho to para isomer ratios of 3:1 and higher, typically greater than 8:1 at conversions greater than 30% based upon aromatic feed, can easily be achieved. In any event the ratio of ortho to para isomer can be enhanced even with those catalyst systems generally suited for the production of high ortho to para ratios. To maximize production of the ortho-alkylated product reactor conditions are monitored and product analysis made. When the rate of decomposition of ortho-alkylated aromatic begins to exceed the rate of formation of ortho-alkylated aromatic amine, the reaction product is withdrawn from the reaction zone. Measurements may be plotted in graph form and rates determined.

Although not intending to be bound by theory, the observed regioselective ortho-alkylation of N-alkylates achieved by the practice of the invention is surprising since from prior art teachings one would expect a free carbenium ion derived from the olefin would result in a thermodynamically favored para-substituted product. Mechanisms were references and Hart-Kosak, J. Org. Chem., 27, 116 (1962) and J. Org. Chem., 22., 1752 (1957). Because of the observed regioselectivity by the practice of this invention we have concluded the ring nitrogen atom must exert a directing influence in forming ortho-alkylated product and this directing influence tends to overcome a counter reaction leading to the thermodynamically favored para-substituted product.

Experiments utilizing appropriately deuterium labelled olefins indicate that the primary mechanism of ortho-alkylation occurs via a concerted reaction between aromatic amine and olefin as shown in Scheme 1. Aniline is used as the illustrative amine and propylene is used as the illustrative olefin.

Scheme 1
Ortho-Alkylation

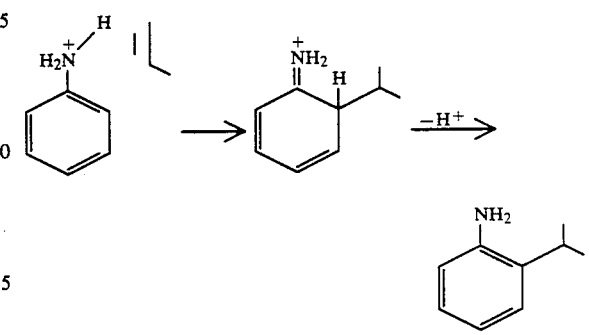

Para-alkylation, on the other hand, occurs differently than ortho-alkylation. Our evidence suggests a significant route to para-alkylation is through transalkylation of aniline via N-isopropylaniline. Scheme 2 below shows this mechanism.

Scheme 2
Para Alkylation

-continued
Scheme 2

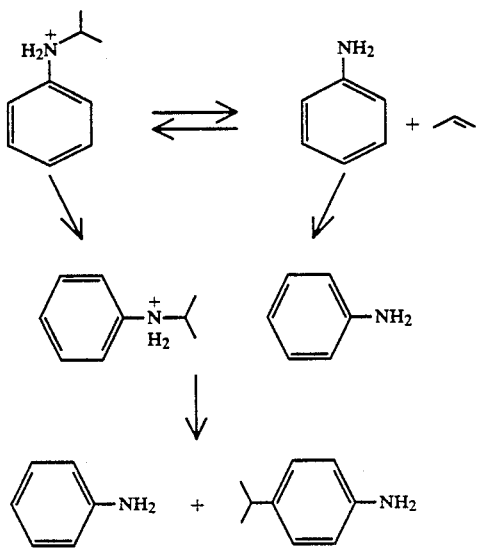

This reaction scheme is supported by experimental work with N-n-propylaniline over 13% Al$_2$O$_3$/87% SiO$_2$, wherein it was found that para-substitution occurred principally on the primary carbon while ortho-substitution occurred at the secondary carbon of the olefin. Although, transalkylation of either the ortho or para ring positions may occur, a clear preference for para alkylation was noted. It is believed the para-regioselectivity may be attributed to steric interference in the transition state as a result of the adjacent amino group. The following Scheme 3 summarizes this experimentation.

Scheme 3

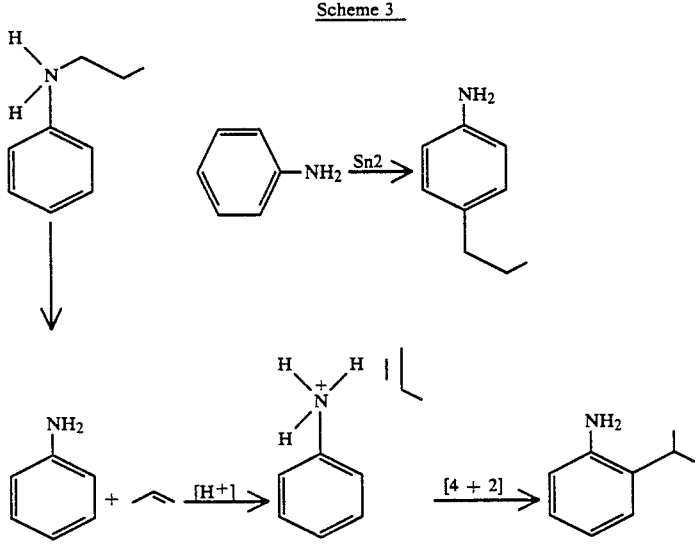

This working mechanism coupled with experimental observation indicates that a high molar ratio of olefin to aromatic amine favors a faster rate of ortho-alkylation of the aromatic amine relative to a slower transalkylation of aromatic amine with aromatic N-alkylate.

These reaction conditions used to produce ortho-alkylated aromatic amine can be summarized as those which use a solid phase acidic catalyst and utilize olefin and pressure to inhibit transalkylation and thereby suppress para formation.

The following examples are provided to illustrate various embodiments of the invention and are not intended to restrict the scope thereof.

EXAMPLE 1

A series of alkylation reactions was carried out in a fixed bed catalytic reactor, the reactor consisting of a 0.5" ID, 304 stainless steel tube which was jacketed with a single-element heater. A 5cc Vicor preheating bed was used to vaporize the reactants as they were passed downflow through the stainless steel tube jacketed reactor. The reactor was of sufficient length to accommodate from about 12-25 cubic centimeters of a solid phase catalyst system, having a particle size of from about 12-18 mesh (U.S. standard size). The reactions were conducted at temperatures ranging from about 100°-400° C. and pressures of from about 50-1000 psig and an LHSV based upon total aromatic amine liquid feed to the vaporizer of from 0.05 to 4.0 hr.$^{-1}$.

The reaction product was collected and byproduct olefin was removed via vaporization. The reaction product then was analyzed (free of olefin) by gas chromatography using an internal standard technique. Results are provided in Tables 1-6.

Temperatures, pressures, catalysts, moles, olefin and amine reactant, and other variables are recited in Table 1. Table 2 provides analytical results with respect to the run conditions described in Table 1. In Table 1 OBS is the sequential line observation for the particular table (there may be some skips); run is an arbitrary run number to permit rapid identification of that data set in other Tables; temperatures is in °C., pressure is in psig, G-Al$_2$O$_3$ refers to gamma-alumina, H-Y is a hydrogen exchanged Y zeolite, 13% Al$_2$O$_3$/SiO$_2$ refers to a silica-alumina catalyst containing 13% by weight of Al$_2$O$_3$. N refers to aromatic amine, i.e., aniline, R refers to olefin, i.e., propylene, X refers to N-alkylate, i.e., N-isopropylaniline, conversion (conv.) is expressed as % and is based upon the total moles ring alkylated product produced divided by the total moles of aromatic amine and N-alkylated amine feed times 100; and o-p, refers to the ortho-para ratio which is the moles of 2+2,6 isomers divided by the moles of 4 isomer+2,4- isomer+2,4,6-isomer. In some cases an ortho to para ratio of >40 has been written in, otherwise one would be dividing by zero. Tables 1 and 2 are arranged on the basis of ascending pressure. Tables 3 and 4 are duplicates of Tables 1 and 2 except they are arranged in ascending conversion. Tables 5 and 6 are duplicates of Tables 1 and 2 except they are arranged in ascending ortho para ratio.

Tables 1-6 illustrate the effect of various process parameters such as the mole ratio of olefin to total aromatic amine as well as the molar ratios of aniline to N-alkylate. They are to be used in combination to observe trends; e.g., O-P ratios vs. conversion based upon reaction parameters. No one specific value is to be considered as controlling but rather is to be considered in combination with another value. The table product legends are as follows:

1. Aniline - aniline
2. N-IPA - N-isopropylaniline
3. 2-IPA - ortho-isopropylaniline
4. 4-IPA - para-isopropylaniline
5. N-2-DIPA - N,2-diisopropylaniline
6. 2,4-DIPA - 2,4-diisopropylaniline
7. 2,6-DIPA - 2,6-diisopropylaniline
8. 2,4,6-TIPA - 2,4,6-triisopropylaniline

TABLE 1

CONVERSION OF N-ISOPROPYLANILINE
ARRANGED IN ASCENDING PRESSURE BY CATALYST TYPE

| OBS | SAMPLE ID | RUN | TEMPERATURE | PRESSURE | Molar Feed Ratio N | R | X | CATALYST TYPE | LHSV* | CONV | O-P |
|---|---|---|---|---|---|---|---|---|---|---|---|
| 1 | 7893-73-88 | 6 | 348 | 30 | 0.50 | 0.00 | 0.50 | G-AL2O3 | 0.13 | 13.92 | 8.13 |
| 2 | 7893-73-89 | 7 | 348 | 30 | 0.50 | 0.00 | 0.50 | G-AL2O3 | 0.13 | 14.38 | 7.93 |
| 3 | 7893-72-83 | 2 | 348 | 30 | 0.00 | 0.00 | 1.00 | G-AL2O3 | 0.13 | 23.58 | 6.40 |
| 4 | 7893-72-82 | 1 | 348 | 30 | 0.00 | 0.00 | 1.00 | G-AL2O3 | 0.13 | 24.16 | 6.37 |
| 5 | 7893-58-52 | 11 | 348 | 860 | 0.00 | 10.00 | 1.00 | G-AL2O3 | 0.13 | 76.80 | 13.74 |
| 6 | 7893-73-86 | 5 | 348 | 900 | 0.50 | 0.00 | 0.50 | G-AL2O3 | 0.13 | 6.97 | >40 |
| 7 | 7893-75-92 | 9 | 348 | 900 | 0.75 | 2.00 | 0.25 | G-AL2O3 | 0.13 | 12.38 | 14.27 |
| 8 | 7893-73-87 | 20 | 349 | 905 | 0.50 | 0.00 | 0.50 | G-AL2O3 | 0.13 | 7.09 | 40.00 |
| 9 | 7893-75-93 | 22 | 349 | 910 | 0.75 | 2.00 | 0.25 | G-AL2O3 | 0.13 | 9.66 | 14.55 |
| 10 | 7893-75-94 | 23 | 349 | 910 | 0.75 | 2.00 | 0.25 | G-AL2O3 | 0.13 | 12.61 | >40 |
| 11 | 7893-74-91 | 8 | 348 | 925 | 0.50 | 2.00 | 0.50 | G-AL2O3 | 0.13 | 32.98 | 31.82 |
| 12 | 7893-74-90 | 21 | 349 | 930 | 0.50 | 2.00 | 0.50 | G-AL2O3 | 0.13 | 19.52 | 35.08 |
| 13 | 7893-72-84 | 3 | 348 | 955 | 0.00 | 2.00 | 1.00 | G-AL2O3 | 0.13 | 28.76 | 24.83 |
| 14 | 7893-71-79 | 18 | 349 | 960 | 0.00 | 0.00 | 1.00 | G-AL2O3 | 0.13 | 30.29 | 8.29 |
| 15 | 7893-71-80 | 19 | 349 | 960 | 0.00 | 0.00 | 1.00 | G-AL2O3 | 0.13 | 30.70 | 8.61 |
| 16 | 7893-72-85 | 4 | 348 | 960 | 0.00 | 2.00 | 1.00 | G-AL2O3 | 0.13 | 40.66 | 19.45 |
| 17 | 7893-53-50 | 10 | 348 | 980 | 0.00 | 6.00 | 1.00 | G-AL2O3 | 0.18 | 62.28 | 14.19 |
| 18 | 7893-60-61 | 15 | 348 | 980 | 0.40 | 10.00 | 0.60 | G-AL2O3 | 0.13 | 80.42 | 19.35 |
| 19 | 7893-59-54 | 12 | 348 | 990 | 0.00 | 10.00 | 1.00 | G-AL2O3 | 0.13 | 77.63 | 14.35 |
| 20 | 7893-59-56 | 13 | 348 | 990 | 0.00 | 10.00 | 1.00 | G-AL2O3 | 0.13 | 78.01 | 15.82 |
| 21 | 7893-60-59 | 14 | 348 | 990 | 0.40 | 10.00 | 0.60 | G-AL2O3 | 0.13 | 81.81 | 15.39 |
| 26 | 7893-61-65 | 17 | 348 | 1000 | 0.40 | 10.00 | 0.60 | G-AL2O3 | 0.13 | 83.85 | 14.57 |
| 27 | 7893-61-63 | 16 | 348 | 1000 | 0.40 | 10.00 | 0.60 | G-AL2O3 | 0.13 | 84.02 | 14.47 |
| 28 | 7723-29-50 | 28 | 247 | 40 | 0.50 | 0.00 | 0.50 | H-Y | 0.18 | 9.44 | 1.08 |
| 29 | 7723-29-51 | 29 | 247 | 40 | 0.50 | 0.00 | 0.50 | H-Y | 0.18 | 9.51 | 1.15 |
| 30 | 7723-30-54 | 32 | 247 | 50 | 0.00 | 0.00 | 1.00 | H-Y | 0.18 | 8.76 | 2.72 |
| 31 | 7723-30-56 | 33 | 247 | 50 | 0.00 | 0.00 | 1.00 | H-Y | 0.18 | 10.01 | 3.49 |
| 32 | 7723-34-72 | 42 | 248 | 994 | 0.50 | 2.00 | 0.50 | H-Y | 0.75 | 21.23 | 8.58 |
| 33 | 7723-34-71 | 41 | 248 | 997 | 0.50 | 2.00 | 0.50 | H-Y | 0.75 | 19.50 | 8.29 |
| 34 | 7723-34-74 | 43 | 248 | 999 | 0.75 | 2.00 | 0.25 | H-Y | 0.75 | 10.40 | 9.43 |

*LHSV based on total aromatic feed only

| OBS | SAMPLE ID | RUN | TEMPERATURE | PRESSURE | Molar Feed Ratio N | R | X | CATALYST TYPE | LHSV | CONV | O-P |
|---|---|---|---|---|---|---|---|---|---|---|---|
| 35 | 7723-33-70 | 40 | 248 | 999 | 0.50 | 2.00 | 0.50 | H-Y | 0.75 | 12.16 | 7.36 |
| 36 | 7723-34-75 | 52 | 249 | 1003 | 0.75 | 2.00 | 0.25 | H-Y | 0.75 | 22.19 | 8.88 |
| 37 | 7723-38-89 | 35 | 247 | 1013 | 0.00 | 0.00 | 1.00 | H-Y | 0.18 | 5.95 | 3.10 |
| 38 | 7723-37-85 | 46 | 248 | 1013 | 0.75 | 2.00 | 0.25 | H-Y | 0.25 | 34.81 | 7.31 |
| 39 | 7723-32-64 | 48 | 249 | 1014 | 0.50 | 2.00 | 0.50 | H-Y | 1.83 | 5.01 | 3.43 |
| 40 | 7723-38-88 | 34 | 247 | 1014 | 0.00 | 0.00 | 1.00 | H-Y | 0.18 | 8.22 | 4.87 |
| 41 | 7723-32-65 | 49 | 249 | 1015 | 0.50 | 2.00 | 0.50 | H-Y | 1.83 | 8.97 | 7.36 |
| 42 | 7723-37-87 | 47 | 248 | 1026 | 0.75 | 2.00 | 0.25 | H-Y | 0.25 | 55.48 | 7.41 |
| 43 | 7723-36-79 | 44 | 248 | 1033 | 0.50 | 2.00 | 0.50 | H-Y | 0.25 | 27.49 | 7.53 |
| 44 | 7723-36-81 | 45 | 248 | 1035 | 0.50 | 2.00 | 0.50 | H-Y | 0.25 | 25.98 | 8.84 |
| 45 | 7723-32-66 | 39 | 248 | 1038 | 0.50 | 2.00 | 0.50 | H-Y | 1.83 | 13.22 | 9.09 |
| 46 | 7723-33-68 | 51 | 249 | 1054 | 0.00 | 2.00 | 1.00 | H-Y | 0.75 | 32.77 | 12.34 |
| 47 | 7723-33-67 | 50 | 249 | 1060 | 0.00 | 2.00 | 1.00 | H-Y | 0.75 | 31.75 | 12.27 |
| 48 | 7723-29-52 | 30 | 247 | 1067 | 0.50 | 0.00 | 0.50 | H-Y | 0.18 | 8.40 | 1.66 |
| 49 | 7723-30-53 | 31 | 247 | 1068 | 0.50 | 0.00 | 0.50 | H-Y | 0.18 | 9.60 | 1.82 |
| 50 | 7723-31-58 | 36 | 248 | 1071 | 0.00 | 2.00 | 1.00 | H-Y | 1.50 | 4.91 | 7.47 |
| 51 | 7723-31-60 | 38 | 248 | 1073 | 0.00 | 2.00 | 1.00 | H-Y | 1.50 | 4.48 | >40 |
| 52 | 7723-31-59 | 37 | 248 | 1076 | 0.00 | 2.00 | 1.00 | H-Y | 1.50 | 4.57 | >40 |
| 53 | 7893-85-12 | 62 | 288 | 30 | 0.50 | 0.00 | 0.50 | 13% AL2O3/SIO2 | 0.18 | 15.53 | 2.63 |
| 54 | 7893-85-11 | 54 | 287 | 30 | 0.50 | 0.00 | 0.50 | 13% AL2O3/SIO2 | 0.18 | 17.16 | 2.63 |
| 55 | 7893-83-06 | 53 | 287 | 30 | 0.00 | 0.00 | 1.00 | 13% AL2O3/SIO2 | 0.18 | 25.08 | 2.34 |
| 56 | 7893-83-05 | 57 | 288 | 30 | 0.00 | 0.00 | 1.00 | 13% AL2O3/SIO2 | 0.18 | 27.87 | 2.30 |
| 61 | 7893-85-13 | 63 | 288 | 890 | 0.50 | 2.00 | 0.50 | 13% AL2O3/SIO2 | 1.17 | 26.69 | 9.26 |
| 62 | 7893-85-14 | 64 | 289 | 890 | 0.50 | 2.00 | 0.50 | 13% AL2O3/SIO2 | 1.17 | 28.99 | 9.17 |
| 63 | 7893-93-15 | 67 | 290 | 930 | 0.75 | 2.00 | 0.25 | 13% AL2O3/SIO2 | 2.20 | 16.97 | 13.39 |
| 64 | 7893-93-16 | 68 | 290 | 930 | 0.75 | 2.00 | 0.25 | 13% AL2O3/SIO2 | 2.20 | 18.73 | 9.12 |
| 65 | 7893-93-17 | 65 | 289 | 930 | 0.75 | 2.00 | 0.25 | 13% AL2O3/SIO2 | 1.10 | 32.45 | 8.44 |

TABLE 1-continued

CONVERSION OF N-ISOPROPYLANILINE
ARRANGED IN ASCENDING PRESSURE BY CATALYST TYPE

| | | | | | | | | | | | |
|---|---|---|---|---|---|---|---|---|---|---|---|
| 66 | 7893-93-18 | 66 | 289 | 930 | 0.75 | 2.00 | 0.25 | 13% AL2O3/SIO2 | 1.10 | 33.83 | 8.28 |
| 67 | 7893-82-03 | 55 | 288 | 970 | 0.00 | 0.00 | 1.00 | 13% AL2O3/SIO2 | 0.18 | 52.45 | 3.64 |
| 68 | 7893-82-04 | 56 | 288 | 975 | 0.00 | 0.00 | 1.00 | 13% AL2O3/SIO2 | 0.18 | 50.67 | 3.83 |

TABLE 2

CONVERSION OF N-ISOPROPYLANILINE

| OBS | RUN | ANILINE MOLE PCT | N-IPA MOLE PCT | 2-IPA MOLE PCT | 4-IPA MOLE PCT | N,2-DIPA MOLE PCT | 2,4-DIPA MOLE PCT | 2,6-DIPA MOLE PCT | 2,4,6-TIPA MOLE PCT | CONV | O-P |
|---|---|---|---|---|---|---|---|---|---|---|---|
| 1 | 6 | 83.98 | 2.10 | 9.21 | 1.13 | 0.00 | 0.00 | 0.00 | 0.00 | 13.92 | 8.13 |
| 2 | 7 | 84.98 | 0.72 | 9.06 | 1.14 | 0.00 | 0.00 | 0.00 | 0.00 | 14.38 | 7.93 |
| 3 | 2 | 74.80 | 1.62 | 13.78 | 1.67 | 0.00 | 0.55 | 0.45 | 0.00 | 23.58 | 6.40 |
| 4 | 1 | 72.91 | 2.93 | 14.07 | 1.69 | 0.00 | 0.60 | 0.51 | 0.00 | 24.16 | 6.37 |
| 5 | 11 | 17.81 | 5.39 | 43.65 | 1.20 | 4.08 | 2.16 | 19.66 | 1.54 | 76.80 | 13.74 |
| 6 | 5 | 56.66 | 36.36 | 3.78 | 0.00 | 0.00 | 0.00 | 0.00 | 0.00 | 6.97 | >40 |
| 7 | 9 | 72.33 | 15.29 | 10.08 | 0.71 | 0.00 | 0.00 | 0.00 | 0.00 | 12.38 | 1427 |
| 8 | 20 | 57.32 | 35.59 | 3.42 | 0.00 | 0.00 | 0.00 | 0.00 | 0.00 | 7.09 | >40 |
| 9 | 22 | 72.59 | 17.75 | 7.42 | 0.51 | 0.00 | 0.00 | 0.00 | 0.00 | 9.66 | 14.55 |
| 10 | 23 | 69.12 | 18.27 | 10.10 | 0.00 | 0.42 | 0.00 | 0.54 | 0.00 | 12.61 | >40 |
| 11 | 8 | 47.84 | 19.18 | 23.67 | 0.00 | 2.36 | 0.98 | 5.23 | 0.00 | 32.98 | 31.82 |
| 12 | 21 | 53.39 | 27.10 | 13.61 | 0.00 | 1.10 | 0.46 | 1.43 | 0.00 | 19.52 | 35.08 |
| 13 | 3 | 41.85 | 29.38 | 18.16 | 0.00 | 2.52 | 0.99 | 3.87 | 0.00 | 28.76 | 24.83 |
| 14 | 18 | 53.34 | 16.37 | 20.75 | 1.66 | 1.78 | 1.23 | 1.47 | 0.00 | 30.29 | 8.29 |
| 15 | 19 | 53.72 | 15.58 | 21.45 | 1.69 | 1.75 | 1.17 | 1.42 | 0.00 | 30.70 | 8.61 |
| 16 | 4 | 40.71 | 18.62 | 26.44 | 0.00 | 3.67 | 1.50 | 7.96 | 0.45 | 40.66 | 19.45 |
| 17 | 10 | 29.42 | 8.30 | 39.30 | 0.73 | 3.60 | 2.02 | 14.30 | 1.28 | 62.28 | 14.19 |
| 18 | 15 | 14.89 | 4.69 | 51.33 | 1.16 | 5.15 | 1.27 | 20.54 | 1.56 | 80.42 | 19.35 |
| 19 | 12 | 16.97 | 5.39 | 48.76 | 1.17 | 4.68 | 2.20 | 18.99 | 1.68 | 77.63 | 14.35 |
| 20 | 13 | 16.68 | 5.31 | 48.24 | 1.07 | 4.88 | 2.15 | 18.78 | 1.32 | 78.01 | 15.82 |
| 21 | 14 | 13.79 | 4.40 | 50.27 | 1.20 | 5.08 | 2.18 | 21.78 | 1.63 | 81.81 | 15.39 |
| 26 | 17 | 12.25 | 3.90 | 50.03 | 1.28 | 5.16 | 2.31 | 23.94 | 1.84 | 83.85 | 14.57 |
| 27 | 16 | 12.11 | 3.88 | 49.54 | 1.30 | 5.11 | 2.29 | 24.18 | 1.87 | 84.02 | 14.47 |
| 28 | 28 | 63.97 | 26.59 | 2.77 | 3.21 | 0.56 | 0.16 | 0.30 | 0.00 | 9.44 | 1.08 |
| 29 | 29 | 62.85 | 27.64 | 2.91 | 3.30 | 0.56 | 0.00 | 0.33 | 0.00 | 9.51 | 1.15 |
| 30 | 32 | 31.18 | 60.06 | 2.80 | 1.40 | 1.63 | 0.42 | 0.54 | 0.00 | 8.76 | 2.72 |
| 31 | 33 | 30.02 | 59.97 | 3.48 | 1.44 | 2.27 | 0.37 | 0.57 | 0.00 | 10.01 | 3.49 |
| 32 | 42 | 55.54 | 23.23 | 14.47 | 1.76 | 2.94 | 0.41 | 1.25 | 0.00 | 21.23 | 8.58 |
| 33 | 41 | 57.77 | 22.74 | 13.02 | 1.65 | 2.53 | 0.35 | 1.04 | 0.00 | 19.50 | 8.29 |
| 34 | 43 | 76.47 | 13.13 | 6.68 | 0.81 | 0.60 | 0.00 | 0.34 | 0.00 | 10.40 | 9.43 |
| 35 | 40 | 66.21 | 21.64 | 7.20 | 1.23 | 1.49 | 0.00 | 0.38 | 0.00 | 12.16 | 7.36 |
| 36 | 52 | 62.87 | 14.94 | 14.48 | 1.51 | 2.16 | 0.62 | 2.33 | 0.00 | 22.19 | 8.88 |
| 37 | 35 | 62.97 | 31.08 | 2.70 | 1.19 | 0.57 | 0.00 | 0.41 | 0.00 | 5.95 | 3.10 |
| 38 | 46 | 49.36 | 15.83 | 19.23 | 1.99 | 3.78 | 1.67 | 6.88 | 0.42 | 34.81 | 7.31 |
| 39 | 48 | 73.31 | 21.68 | 1.82 | 0.64 | 0.39 | 0.00 | 0.00 | 0.00 | 5.01 | 3.43 |
| 40 | 34 | 61.14 | 30.63 | 3.57 | 1.15 | 1.03 | 0.00 | 0.99 | 0.00 | 8.22 | 4.87 |
| 41 | 49 | 68.30 | 22.72 | 5.50 | 0.90 | 1.15 | 0.00 | 0.00 | 0.00 | 8.97 | 7.36 |
| 42 | 47 | 25.90 | 18.62 | 28.29 | 2.62 | 7.13 | 3.21 | 13.11 | 0.73 | 55.48 | 7.41 |
| 43 | 44 | 50.34 | 22.18 | 18.56 | 2.41 | 3.66 | 0.85 | 2.33 | 0.00 | 27.49 | 7.53 |
| 44 | 45 | 51.09 | 22.93 | 14.94 | 1.64 | 3.79 | 0.91 | 3.84 | 0.00 | 25.98 | 8.84 |
| 45 | 39 | 63.70 | 23.09 | 7.96 | 1.11 | 1.75 | 0.00 | 0.38 | 0.00 | 13.22 | 9.09 |
| 46 | 51 | 30.32 | 36.91 | 16.18 | 1.46 | 10.00 | 1.03 | 4.49 | 0.00 | 32.77 | 12.34 |
| 47 | 50 | 31.37 | 36.88 | 16.46 | 1.44 | 8.87 | 0.97 | 4.22 | 0.00 | 31.75 | 12.27 |
| 48 | 30 | 52.21 | 39.39 | 2.97 | 2.32 | 0.88 | 0.00 | 0.00 | 0.00 | 8.40 | 1.66 |
| 49 | 31 | 53.29 | 37.12 | 3.63 | 2.72 | 1.00 | 0.00 | 0.32 | 0.00 | 9.60 | 1.82 |
| 50 | 36 | 38.39 | 56.70 | 1.80 | 0.48 | 1.79 | 0.00 | 0.00 | 0.00 | 4.91 | 7.47 |
| 51 | 38 | 40.17 | 55.34 | 1.80 | 0.00 | 1.53 | 0.00 | 0.00 | 0.00 | 4.48 | >40 |
| 52 | 37 | 40.23 | 55.20 | 1.75 | 0.00 | 1.60 | 0.00 | 0.00 | 0.00 | 4.57 | >40 |
| 53 | 62 | 76.44 | 8.03 | 11.61 | 3.30 | 0.63 | 1.72 | 0.97 | 0.00 | 15.53 | 2.63 |
| 54 | 54 | 76.09 | 6.75 | 12.67 | 3.51 | 0.61 | 1.96 | 1.12 | 0.00 | 17.16 | 2.63 |
| 55 | 53 | 60.45 | 14.47 | 14.47 | 3.86 | 2.00 | 3.39 | 2.15 | 0.71 | 25.08 | 2.34 |
| 56 | 57 | 58.88 | 13.25 | 14.40 | 3.73 | 1.95 | 3.57 | 2.29 | 0.80 | 27.87 | 2.30 |
| 61 | 63 | 42.05 | 31.26 | 11.34 | 1.22 | 6.76 | 0.93 | 1.80 | 0.00 | 26.69 | 9.26 |
| 62 | 64 | 40.48 | 30.52 | 13.14 | 1.38 | 7.61 | 1.13 | 2.21 | 0.00 | 28.99 | 9.17 |
| 63 | 67 | 63.67 | 19.35 | 11.48 | 1.16 | 3.04 | 0.00 | 1.00 | 0.00 | 16.97 | 13.39 |
| 64 | 68 | 61.67 | 19.61 | 12.21 | 1.23 | 3.29 | 0.60 | 1.18 | 0.00 | 18.73 | 9.12 |
| 65 | 65 | 48.47 | 19.08 | 19.44 | 1.58 | 5.41 | 1.53 | 3.56 | 0.26 | 32.45 | 8.44 |
| 66 | 66 | 46.95 | 19.22 | 19.74 | 1.56 | 5.74 | 1.68 | 3.81 | 0.29 | 33.83 | 8.28 |
| 67 | 55 | 33.23 | 14.33 | 24.96 | 2.80 | 6.47 | 5.92 | 7.15 | 1.88 | 52.45 | 3.64 |
| 68 | 56 | 33.28 | 16.05 | 24.31 | 2.95 | 7.35 | 5.49 | 6.86 | 1.63 | 50.67 | 3.83 |

TABLE 3

CONVERSION OF N-ISOPROPYLANILINE
ARRANGED IN ASCENDING CONVERSION BY CATALYST TYPE

| OBS | SAMPLE ID | RUN | TEMPERATURE | PRESSURE | N | R | X | CATALYST TYPE | LHSV | CONV | O-P |
|---|---|---|---|---|---|---|---|---|---|---|---|
| 1 | 7893-73-86 | 5 | 348 | 900 | 0.50 | 0.00 | 0.50 | G-AL2O3 | 0.13 | 6.97 | >40 |
| 2 | 7893-73-87 | 20 | 349 | 905 | 0.50 | 0.00 | 0.50 | G-AL2O3 | 0.13 | 7.09 | >40 |
| 3 | 7893-75-93 | 22 | 349 | 910 | 0.75 | 2.00 | 0.25 | G-AL2O3 | 0.13 | 9.66 | 14.55 |
| 4 | 7893-75-92 | 9 | 348 | 900 | 0.75 | 2.00 | 0.25 | G-AL2O3 | 0.13 | 12.38 | 14.27 |
| 5 | 7893-75-94 | 23 | 349 | 910 | 0.75 | 2.00 | 0.25 | G-AL2O3 | 0.13 | 12.61 | >40 |
| 6 | 7893-73-88 | 6 | 348 | 30 | 0.50 | 0.00 | 0.50 | G-AL2O3 | 0.13 | 13.92 | 8.13 |
| 7 | 7893-73-89 | 7 | 348 | 30 | 0.50 | 0.00 | 0.50 | G-AL2O3 | 0.13 | 14.38 | 7.93 |
| 8 | 7893-74-90 | 21 | 349 | 930 | 0.50 | 2.00 | 0.50 | G-AL2O3 | 0.13 | 19.52 | 35.08 |
| 9 | 7893-72-83 | 2 | 348 | 30 | 0.00 | 0.00 | 1.00 | G-AL2O3 | 0.13 | 23.58 | 6.40 |
| 10 | 7893-72-82 | 1 | 348 | 30 | 0.00 | 0.00 | 1.00 | G-AL2O3 | 0.13 | 24.16 | 6.37 |
| 11 | 7893-72-84 | 3 | 348 | 955 | 0.00 | 2.00 | 1.00 | G-AL2O3 | 0.13 | 28.76 | 24.83 |
| 12 | 7893-71-79 | 18 | 349 | 960 | 0.00 | 0.00 | 1.00 | G-AL2O3 | 0.13 | 30.29 | 8.29 |
| 13 | 7893-71-80 | 19 | 349 | 960 | 0.00 | 0.00 | 1.00 | G-AL2O3 | 0.13 | 30.70 | 8.61 |
| 14 | 7893-74-91 | 8 | 348 | 925 | 0.50 | 2.00 | 0.50 | G-AL2O3 | 0.13 | 32.98 | 31.82 |
| 15 | 7893-72-85 | 4 | 348 | 960 | 0.00 | 2.00 | 1.00 | G-AL2O3 | 0.13 | 40.66 | 19.45 |
| 20 | 7893-53-50 | 10 | 348 | 980 | 0.00 | 6.90 | 1.00 | G-AL2O3 | 0.18 | 62.28 | 14.19 |
| 21 | 7893-58-52 | 11 | 348 | 860 | 0.00 | 10.00 | 1.00 | G-AL2O3 | 0.13 | 76.80 | 13.74 |
| 22 | 7893-59-54 | 12 | 348 | 990 | 0.00 | 10.00 | 1.00 | G-AL2O3 | 0.13 | 77.63 | 14.35 |
| 23 | 7893-59-56 | 13 | 348 | 990 | 0.00 | 10.00 | 1.00 | G-AL2O3 | 0.13 | 78.01 | 15.82 |
| 24 | 7893-60-61 | 15 | 348 | 980 | 0.40 | 10.00 | 0.60 | G-AL2O3 | 0.13 | 80.42 | 19.35 |
| 25 | 7893-60-59 | 14 | 348 | 990 | 0.40 | 10.00 | 0.60 | G-AL2O3 | 0.13 | 81.81 | 15.39 |
| 26 | 7893-61-65 | 17 | 348 | 1000 | 0.40 | 10.00 | 0.60 | G-AL2O3 | 0.13 | 83.85 | 14.57 |
| 27 | 7893-61-63 | 16 | 348 | 1000 | 0.40 | 10.00 | 0.60 | G-AL2O3 | 0.13 | 84.02 | 14.47 |
| 28 | 7723-31-60 | 38 | 248 | 1073 | 0.00 | 2.00 | 1.00 | H-Y | 1.50 | 4.48 | >40 |
| 29 | 7723-31-59 | 37 | 248 | 1076 | 0.00 | 2.00 | 1.00 | H-Y | 1.50 | 4.57 | >40 |
| 30 | 7723-31-58 | 36 | 248 | 1071 | 0.00 | 2.00 | 1.00 | H-Y | 1.50 | 4.91 | 747 |
| 31 | 7723-32-64 | 48 | 249 | 1014 | 0.50 | 2.00 | 0.50 | H-Y | 1.83 | 5.01 | 3.43 |
| 32 | 7723-38-89 | 35 | 247 | 1013 | 0.00 | 0.00 | 1.00 | H-Y | 0.18 | 5.95 | 3.10 |
| 33 | 7723-38-88 | 34 | 247 | 1014 | 0.00 | 0.00 | 1.00 | H-Y | 0.18 | 8.22 | 4.87 |
| 34 | 7723-29-52 | 30 | 247 | 1067 | 0.50 | 0.00 | 0.50 | H-Y | 0.18 | 8.40 | 1.66 |
| 35 | 7723-30-54 | 32 | 247 | 50 | 0.00 | 0.00 | 1.00 | H-Y | 0.18 | 8.76 | 2.72 |
| 36 | 7723-32-65 | 49 | 249 | 1015 | 0.50 | 2.00 | 0.50 | H-Y | 1.83 | 8.97 | 7.36 |
| 37 | 7723-29-50 | 28 | 247 | 40 | 0.50 | 0.00 | 0.50 | H-Y | 0.18 | 9.44 | 1.08 |
| 38 | 7723-29-51 | 29 | 247 | 40 | 0.50 | 0.00 | 0.50 | H-Y | 0.18 | 9.51 | 1.15 |
| 39 | 7723-30-53 | 31 | 247 | 1068 | 0.50 | 0.00 | 0.50 | H-Y | 0.18 | 9.60 | 1.82 |
| 40 | 7723-30-56 | 33 | 247 | 50 | 0.00 | 0.00 | 1.00 | H-Y | 0.18 | 10.01 | 3.49 |
| 41 | 7723-34-74 | 43 | 248 | 999 | 0.75 | 2.00 | 0.25 | H-Y | 0.75 | 10.40 | 9.43 |
| 42 | 7723-33-70 | 40 | 248 | 999 | 0.50 | 2.00 | 0.50 | H-Y | 0.75 | 12.16 | 7.36 |
| 43 | 7723-32-66 | 39 | 248 | 1038 | 0.50 | 2.00 | 0.50 | H-Y | 1.83 | 13.22 | 9.09 |
| 44 | 7723-34-71 | 41 | 248 | 997 | 0.50 | 2.00 | 0.50 | H-Y | 0.75 | 19.50 | 8.29 |
| 45 | 7723-34-72 | 42 | 248 | 994 | 0.50 | 2.00 | 0.50 | H-Y | 0.75 | 21.23 | 8.58 |
| 46 | 7723-34-75 | 52 | 249 | 1003 | 0.75 | 2.00 | 0.25 | H-Y | 0.75 | 22.19 | 8.88 |
| 47 | 7723-36-81 | 45 | 248 | 1035 | 0.50 | 2.00 | 0.50 | H-Y | 0.25 | 25.98 | 8.84 |
| 48 | 7723-36-79 | 44 | 248 | 1033 | 0.50 | 2.00 | 0.50 | H-Y | 0.25 | 27.49 | 7.53 |
| 49 | 7723-33-67 | 50 | 249 | 1060 | 0.00 | 2.00 | 1.00 | H-Y | 0.75 | 31.75 | 12.27 |
| 50 | 7723-33-68 | 51 | 249 | 1054 | 0.00 | 2.00 | 1.00 | H-Y | 0.75 | 32.77 | 12.34 |
| 51 | 7723-37-85 | 46 | 248 | 1013 | 0.75 | 2.00 | 0.25 | H-Y | 0.25 | 34.81 | 7.31 |
| 52 | 7723-37-87 | 47 | 248 | 1026 | 0.75 | 2.00 | 0.25 | H-Y | 0.25 | 55.48 | 7.41 |
| 53 | 7893-85-12 | 62 | 288 | 30 | 0.50 | 0.00 | 0.50 | 13% AL2O3/SIO2 | 0.18 | 15.53 | 2.63 |
| 54 | 7893-93-15 | 67 | 290 | 930 | 0.75 | 2.00 | 0.25 | 13% AL2O3/SIO2 | 2.20 | 16.97 | 13.39 |
| 55 | 7893-85-11 | 54 | 287 | 30 | 0.50 | 0.00 | 0.50 | 13% AL2O3/SIO2 | 0.18 | 17.16 | 2.63 |
| 57 | 7893-93-16 | 68 | 290 | 930 | 0.75 | 2.00 | 0.25 | 13% AL2O3/SIO2 | 2.20 | 18.73 | 9.12 |
| 59 | 7893-83-06 | 53 | 287 | 30 | 0.00 | 0.00 | 1.00 | 13% AL2O3/SIO2 | 0.18 | 25.08 | 2.34 |
| 60 | 7893-85-13 | 63 | 288 | 890 | 0.50 | 2.00 | 0.50 | 13% AL2O3/SIO2 | 1.17 | 26.69 | 9.26 |
| 61 | 7893-83-05 | 57 | 288 | 30 | 0.00 | 0.00 | 1.00 | 13% AL2O3/SIO2 | 0.18 | 27.87 | 2.30 |
| 62 | 7893-85-14 | 64 | 289 | 890 | 0.50 | 2.00 | 0.50 | 13% AL2O3/SIO2 | 1.17 | 28.99 | 9.17 |
| 63 | 7893-93-17 | 65 | 289 | 930 | 0.75 | 2.00 | 0.25 | 13% AL2O3/SIO2 | 1.10 | 32.45 | 8.44 |
| 64 | 7893-93-18 | 66 | 289 | 930 | 0.75 | 2.00 | 0.25 | 13% AL2O3/SIO2 | 1.10 | 33.83 | 8.28 |
| 65 | 7893-82-04 | 56 | 288 | 975 | 0.00 | 0.00 | 1.00 | 13% AL2O3/SIO2 | 0.18 | 50.67 | 3.83 |
| 66 | 7893-82-03 | 55 | 288 | 970 | 0.00 | 0.00 | 1.00 | 13% AL2O3/SIO2 | 0.18 | 52.45 | 3.64 |

TABLE 4

CONVERSION OF N-ISOPROPYLANILINE

| OBS | RUN | ANILINE MOLE PCT | N-IPA MOLE PCT | 2-IPA MOLE PCT | 4-IPA MOLE PCT | N,2-DIPA MOLE PCT | 2,4-DIPA MOLE PCT | 2,6-DIPA MOLE PCT | 2,4,6-TIPA MOLE PCT | CONV | O-P |
|---|---|---|---|---|---|---|---|---|---|---|---|
| 1 | 5 | 56.66 | 36.36 | 3.78 | 0.00 | 0.00 | 0.00 | 0.00 | 0.00 | 6.97 | >40 |
| 2 | 20 | 57.32 | 35.59 | 3.42 | 0.00 | 0.00 | 0.00 | 0.00 | 0.00 | 7.09 | >40 |
| 3 | 22 | 72.59 | 17.75 | 7.42 | 0.51 | 0.00 | 0.00 | 0.00 | 0.00 | 9.66 | 14.55 |
| 4 | 9 | 72.33 | 15.29 | 10.08 | 0.71 | 0.00 | 0.00 | 0.00 | 0.00 | 12.38 | 14.27 |
| 5 | 23 | 69.12 | 18.27 | 10.10 | 0.00 | 0.42 | 0.00 | 0.54 | 0.00 | 12.61 | >40 |
| 6 | 6 | 83.98 | 2.10 | 9.21 | 1.13 | 0.00 | 0.00 | 0.00 | 0.00 | 13.92 | 8.13 |
| 7 | 7 | 84.89 | 0.72 | 9.06 | 1.14 | 0.00 | 0.00 | 0.00 | 0.00 | 14.38 | 7.93 |
| 8 | 21 | 53.39 | 27.10 | 13.61 | 0.00 | 1.10 | 0.46 | 1.43 | 0.00 | 19.52 | 35.08 |

TABLE 4-continued

CONVERSION OF N-ISOPROPYLANILINE

| OBS | RUN | ANILINE MOLE PCT | N-IPA MOLE PCT | 2-IPA MOLE PCT | 4-IPA MOLE PCT | N,2-DIPA MOLE PCT | 2,4-DIPA MOLE PCT | 2,6-DIPA MOLE PCT | 2,4,6-TIPA MOLE PCT | CONV | O-P |
|---|---|---|---|---|---|---|---|---|---|---|---|
| 9 | 2 | 74.80 | 1.62 | 13.78 | 1.67 | 0.00 | 0.55 | 0.45 | 0.00 | 23.58 | 6.40 |
| 10 | 1 | 72.91 | 2.93 | 14.07 | 1.69 | 0.00 | 0.60 | 0.51 | 0.00 | 24.16 | 6.37 |
| 11 | 3 | 41.85 | 29.38 | 18.16 | 0.00 | 2.52 | 0.99 | 3.87 | 0.00 | 28.76 | 24.83 |
| 12 | 18 | 53.34 | 16.37 | 20.75 | 1.66 | 1.78 | 1.23 | 1.47 | 0.00 | 30.29 | 8.29 |
| 13 | 19 | 53.72 | 15.58 | 21.45 | 1.69 | 1.75 | 1.17 | 1.42 | 0.00 | 30.70 | 8.61 |
| 14 | 8 | 47.84 | 19.18 | 23.67 | 0.00 | 2.36 | 0.98 | 5.23 | 0.00 | 32.98 | 31.82 |
| 15 | 4 | 40.71 | 18.62 | 26.44 | 0.00 | 3.67 | 1.50 | 7.96 | 0.45 | 40.66 | 19.45 |
| 20 | 10 | 29.42 | 8.30 | 39.30 | 0.73 | 3.60 | 2.02 | 14.30 | 1.28 | 62.28 | 14.19 |
| 21 | 11 | 17.81 | 5.39 | 43.65 | 1.20 | 4.08 | 2.16 | 19.66 | 1.54 | 76.80 | 13.74 |
| 22 | 12 | 16.97 | 5.39 | 48.76 | 1.17 | 4.68 | 2.20 | 18.99 | 1.68 | 77.63 | 14.35 |
| 23 | 13 | 16.68 | 5.31 | 48.24 | 1.07 | 4.88 | 2.15 | 18.78 | 1.32 | 78.01 | 15.82 |
| 24 | 15 | 14.89 | 4.69 | 51.33 | 1.16 | 5.15 | 1.27 | 20.54 | 1.56 | 80.42 | 19.35 |
| 25 | 14 | 13.79 | 4.40 | 50.27 | 1.20 | 5.08 | 2.18 | 21.78 | 1.63 | 81.81 | 15.39 |
| 26 | 17 | 12.25 | 3.90 | 50.03 | 1.28 | 5.16 | 2.31 | 23.94 | 1.84 | 83.85 | 14.57 |
| 27 | 16 | 12.11 | 3.88 | 49.54 | 1.30 | 5.11 | 2.29 | 24.18 | 1.87 | 84.02 | 14.47 |
| 28 | 38 | 40.17 | 55.34 | 1.80 | 0.00 | 1.53 | 0.00 | 0.00 | 0.00 | 4.48 | >40 |
| 29 | 37 | 40.23 | 55.20 | 1.75 | 0.00 | 1.60 | 0.00 | 0.00 | 0.00 | 4.57 | >40 |
| 30 | 36 | 38.39 | 56.70 | 1.80 | 0.48 | 1.79 | 0.00 | 0.00 | 0.00 | 4.91 | 7.47 |
| 31 | 48 | 73.31 | 21.68 | 1.82 | 0.64 | 0.39 | 0.00 | 0.00 | 0.00 | 5.01 | 3.43 |
| 32 | 35 | 62.97 | 31.08 | 2.70 | 1.19 | 0.57 | 0.00 | 0.41 | 0.00 | 5.95 | 3.10 |
| 33 | 34 | 61.14 | 30.63 | 3.57 | 1.15 | 1.03 | 0.00 | 0.99 | 0.00 | 8.22 | 4.87 |
| 34 | 30 | 52.21 | 39.39 | 2.97 | 2.32 | 0.88 | 0.00 | 0.00 | 0.00 | 8.40 | 1.66 |
| 35 | 32 | 31.18 | 60.06 | 2.80 | 1.40 | 1.63 | 0.42 | 0.54 | 0.00 | 8.76 | 2.72 |
| 36 | 49 | 68.30 | 22.72 | 5.50 | 0.90 | 1.15 | 0.00 | 0.00 | 0.00 | 8.97 | 7.36 |
| 37 | 28 | 63.97 | 26.59 | 2.77 | 3.21 | 0.56 | 0.16 | 0.30 | 0.00 | 9.44 | 1.08 |
| 38 | 29 | 62.85 | 27.64 | 2.91 | 3.30 | 0.56 | 0.00 | 0.33 | 0.00 | 9.51 | 1.15 |
| 39 | 31 | 53.29 | 37.12 | 3.63 | 2.72 | 1.00 | 0.00 | 0.32 | 0.00 | 9.60 | 1.82 |
| 40 | 33 | 30.02 | 59.97 | 3.48 | 1.44 | 2.27 | 0.37 | 0.57 | 0.00 | 10.01 | 3.49 |
| 41 | 43 | 76.47 | 13.13 | 6.68 | 0.81 | 0.60 | 0.00 | 0.34 | 0.00 | 10.40 | 9.43 |
| 42 | 40 | 66.21 | 21.64 | 7.20 | 1.23 | 1.49 | 0.00 | 0.38 | 0.00 | 12.16 | 7.36 |
| 43 | 39 | 63.70 | 23.09 | 7.96 | 1.11 | 1.75 | 0.00 | 0.38 | 0.00 | 13.22 | 9.09 |
| 44 | 41 | 57.77 | 22.74 | 13.02 | 1.65 | 2.53 | 0.35 | 1.04 | 0.00 | 19.50 | 8.29 |
| 45 | 42 | 55.54 | 23.23 | 14.47 | 1.76 | 2.94 | 0.41 | 1.25 | 0.00 | 21.23 | 8.58 |
| 46 | 52 | 62.87 | 14.94 | 14.48 | 1.51 | 2.16 | 0.62 | 2.33 | 0.00 | 22.19 | 8.88 |
| 47 | 45 | 51.09 | 22.93 | 14.94 | 1.64 | 3.79 | 0.91 | 3.84 | 0.00 | 25.98 | 8.84 |
| 48 | 44 | 50.34 | 22.18 | 18.56 | 2.41 | 3.66 | 0.85 | 2.33 | 0.00 | 27.49 | 7.53 |
| 49 | 50 | 31.37 | 36.88 | 16.46 | 1.44 | 8.87 | 0.97 | 4.22 | 0.00 | 31.75 | 12.27 |
| 50 | 51 | 30.32 | 36.91 | 16.18 | 1.46 | 10.00 | 1.03 | 4.49 | 0.00 | 32.77 | 12.34 |
| 51 | 46 | 49.36 | 15.83 | 19.23 | 1.99 | 3.78 | 1.67 | 6.88 | 0.42 | 34.81 | 7.31 |
| 52 | 47 | 25.90 | 18.62 | 28.29 | 2.62 | 7.13 | 3.21 | 13.11 | 0.73 | 55.48 | 7.41 |
| 53 | 62 | 76.44 | 8.03 | 11.61 | 3.30 | 0.63 | 1.72 | 0.97 | 0.00 | 15.53 | 2.63 |
| 54 | 67 | 63.67 | 19.35 | 11.48 | 1.16 | 3.04 | 0.00 | 1.00 | 0.00 | 16.97 | 13.39 |
| 55 | 54 | 76.09 | 6.75 | 12.67 | 3.51 | 0.61 | 1.96 | 1.12 | 0.00 | 17.16 | 2.63 |
| 57 | 68 | 61.67 | 19.61 | 12.21 | 1.23 | 3.29 | 0.60 | 1.18 | 0.00 | 18.73 | 9.12 |
| 59 | 53 | 60.45 | 14.47 | 14.47 | 3.86 | 2.00 | 3.39 | 2.15 | 0.71 | 25.08 | 2.34 |
| 60 | 63 | 42.05 | 31.26 | 11.34 | 1.22 | 6.76 | 0.93 | 1.80 | 0.00 | 26.69 | 9.26 |
| 61 | 57 | 58.88 | 13.25 | 14.40 | 3.73 | 1.95 | 3.57 | 2.29 | 0.80 | 27.87 | 2.30 |
| 62 | 64 | 40.48 | 30.52 | 13.14 | 1.39 | 7.61 | 1.13 | 2.21 | 0.00 | 28.99 | 9.17 |
| 63 | 65 | 48.47 | 19.08 | 19.44 | 1.58 | 5.41 | 1.53 | 3.56 | 0.26 | 32.45 | 8.44 |
| 64 | 66 | 46.95 | 19.22 | 19.74 | 1.56 | 5.74 | 1.68 | 3.81 | 0.29 | 33.83 | 8.28 |
| 65 | 56 | 33.28 | 16.05 | 24.31 | 2.95 | 7.35 | 5.49 | 6.86 | 1.63 | 50.67 | 3.83 |
| 66 | 55 | 33.23 | 14.33 | 24.96 | 2.80 | 6.47 | 5.92 | 7.15 | 1.88 | 52.45 | 3.64 |

TABLE 5

CONVERSION OF N-ISOPROPYLANILINE ARRANGED IN ASCENDING ORTHO-PARA RATIO BY CATALYST TYPE

| OBS | SAMPLE ID | RUN | TEMPERATURE | PRESSURE | Molar Feed Ratio N | Molar Feed Ratio R | Molar Feed Ratio X | CATALYST TYPE | LHSV | CONV | O-P |
|---|---|---|---|---|---|---|---|---|---|---|---|
| 1 | 7893-73-86 | 5 | 348 | 900 | 0.50 | 0.00 | 0.50 | G-AL2O3 | 0.13 | 6.97 | >40 |
| 2 | 7893-73-87 | 20 | 349 | 905 | 0.50 | 0.00 | 0.50 | G-AL2O3 | 0.13 | 7.09 | >40 |
| 3 | 7893-75-94 | 23 | 349 | 910 | 0.75 | 2.00 | 0.25 | G-AL2O3 | 0.13 | 12.61 | >40 |
| 4 | 7893-72-82 | 1 | 348 | 30 | 0.00 | 0.00 | 1.00 | G-AL2O3 | 0.13 | 24.16 | 6.37 |
| 5 | 7893-72-83 | 2 | 348 | 30 | 0.00 | 0.00 | 1.00 | G-AL2O3 | 0.13 | 23.58 | 6.40 |
| 8 | 7893-73-89 | 7 | 348 | 30 | 0.50 | 0.00 | 0.50 | G-AL2O3 | 0.13 | 14.38 | 7.93 |
| 9 | 7893-73-88 | 6 | 348 | 30 | 0.50 | 0.00 | 0.50 | G-AL2O3 | 0.13 | 13.92 | 8.13 |
| 10 | 7893-71-79 | 18 | 349 | 960 | 0.00 | 0.00 | 1.00 | G-AL2O3 | 0.13 | 30.29 | 8.29 |
| 12 | 7893-71-80 | 19 | 349 | 960 | 0.00 | 0.00 | 1.00 | G-AL2O3 | 0.13 | 30.70 | 8.61 |
| 14 | 7893-58-52 | 11 | 348 | 860 | 0.00 | 10.00 | 1.00 | G-AL2O3 | 0.13 | 76.80 | 13.74 |
| 15 | 7893-53-50 | 10 | 348 | 980 | 0.00 | 6.90 | 1.00 | G-AL2O3 | 0.18 | 62.28 | 14.19 |
| 16 | 7893-75-92 | 9 | 348 | 900 | 0.75 | 2.00 | 0.25 | G-AL2O3 | 0.13 | 12.38 | 14.27 |
| 17 | 7893-59-54 | 12 | 348 | 990 | 0.00 | 10.00 | 1.00 | G-AL2O3 | 0.13 | 77.63 | 14.35 |
| 18 | 7893-61-63 | 16 | 348 | 1000 | 0.40 | 10.00 | 0.60 | G-AL2O3 | 0.13 | 84.02 | 14.47 |
| 19 | 7893-75-93 | 22 | 349 | 910 | 0.75 | 2.00 | 0.25 | G-AL2O3 | 0.13 | 9.66 | 14.55 |
| 20 | 7893-61-65 | 17 | 348 | 1000 | 0.40 | 10.00 | 0.60 | G-AL2O3 | 0.13 | 83.85 | 14.57 |

TABLE 5-continued
CONVERSION OF N-ISOPROPYLANILINE
ARRANGED IN ASCENDING ORTHO-PARA RATIO BY CATALYST TYPE

| OBS | SAMPLE ID | RUN | TEMPERATURE | PRESSURE | Molar Feed Ratio N | R | X | CATALYST TYPE | LHSV | CONV | O-P |
|---|---|---|---|---|---|---|---|---|---|---|---|
| 21 | 7893-60-59 | 14 | 348 | 990 | 0.40 | 10.00 | 0.60 | G-AL2O3 | 0.13 | 81.81 | 15.39 |
| 22 | 7893-59-56 | 13 | 348 | 990 | 0.00 | 10.00 | 1.00 | G-AL2O3 | 0.13 | 78.01 | 15.82 |
| 23 | 7893-60-61 | 15 | 348 | 980 | 0.40 | 10.00 | 0.60 | G-AL2O3 | 0.13 | 80.42 | 19.35 |
| 24 | 7893-72-85 | 4 | 348 | 960 | 0.00 | 2.00 | 1.00 | G-AL2O3 | 0.13 | 40.66 | 19.45 |
| 25 | 7893-72-84 | 3 | 348 | 955 | 0.00 | 2.00 | 1.00 | G-AL2O3 | 0.13 | 28.76 | 24.83 |
| 26 | 7893-74-91 | 8 | 348 | 925 | 0.50 | 2.00 | 0.50 | G-AL2O3 | 0.13 | 32.98 | 31.82 |
| 27 | 7893-74-90 | 21 | 349 | 930 | 0.50 | 2.00 | 0.50 | G-AL2O3 | 0.13 | 19.52 | 35.08 |
| 28 | 7723-31-59 | 37 | 248 | 1076 | 0.00 | 2.00 | 1.00 | H-Y | 1.50 | 4.57 | >40 |
| 29 | 7723-31-60 | 38 | 248 | 1073 | 0.00 | 2.00 | 1.00 | H-Y | 1.50 | 4.48 | >40 |
| 30 | 7723-29-50 | 28 | 247 | 40 | 0.50 | 0.00 | 0.50 | H-Y | 0.18 | 9.44 | 1.08 |
| 31 | 7723-29-51 | 29 | 247 | 40 | 0.50 | 0.00 | 0.50 | H-Y | 0.18 | 9.51 | 1.15 |
| 32 | 7723-29-52 | 30 | 247 | 1067 | 0.50 | 0.00 | 0.50 | H-Y | 0.18 | 8.40 | 1.66 |
| 33 | 7723-30-53 | 31 | 247 | 1068 | 0.50 | 0.00 | 0.50 | H-Y | 0.18 | 9.60 | 1.82 |
| 34 | 7723-30-54 | 32 | 247 | 50 | 0.00 | 0.00 | 1.00 | H-Y | 0.18 | 8.76 | 2.72 |
| 35 | 7723-38-89 | 35 | 247 | 1013 | 0.00 | 0.00 | 1.00 | H-Y | 0.18 | 5.95 | 3.10 |
| 36 | 7723-32-64 | 48 | 249 | 1014 | 0.50 | 2.00 | 0.50 | H-Y | 1.83 | 5.01 | 3.43 |
| 37 | 7723-30-56 | 33 | 247 | 50 | 0.00 | 0.00 | 1.00 | H-Y | 0.18 | 10.01 | 3.49 |
| 38 | 7723-38-88 | 34 | 247 | 1014 | 0.00 | 0.00 | 1.00 | H-Y | 0.18 | 8.22 | 4.87 |
| 39 | 7723-37-85 | 46 | 248 | 1013 | 0.75 | 2.00 | 0.25 | H-Y | 0.25 | 34.81 | 7.31 |
| 40 | 7723-33-70 | 40 | 248 | 999 | 0.50 | 2.00 | 0.50 | H-Y | 0.75 | 12.16 | 7.36 |
| 41 | 7723-32-65 | 49 | 249 | 1015 | 0.50 | 2.00 | 0.50 | H-Y | 1.83 | 8.97 | 7.36 |
| 42 | 7723-37-87 | 47 | 248 | 1026 | 0.75 | 2.00 | 0.25 | H-Y | 0.25 | 55.48 | 7.41 |
| 43 | 7723-31-58 | 36 | 248 | 1071 | 0.00 | 2.00 | 1.00 | H-Y | 1.50 | 4.91 | 7.47 |
| 44 | 7723-36-79 | 44 | 248 | 1033 | 0.50 | 2.00 | 0.50 | H-Y | 0.25 | 27.49 | 7.53 |
| 45 | 7723-34-71 | 41 | 248 | 997 | 0.50 | 2.00 | 0.50 | H-Y | 0.75 | 19.50 | 8.29 |
| 46 | 7723-34-72 | 42 | 248 | 994 | 0.50 | 2.00 | 0.50 | H-Y | 0.75 | 21.23 | 8.58 |
| 47 | 7723-36-81 | 45 | 248 | 1035 | 0.50 | 2.00 | 0.50 | H-Y | 0.25 | 25.98 | 8.84 |
| 48 | 7723-34-75 | 52 | 249 | 1003 | 0.75 | 2.00 | 0.25 | H-Y | 0.75 | 22.19 | 8.88 |
| 49 | 7723-32-66 | 39 | 248 | 1038 | 0.50 | 2.00 | 0.50 | H-Y | 1.83 | 13.22 | 9.09 |
| 50 | 7723-34-74 | 43 | 248 | 999 | 0.75 | 2.00 | 0.25 | H-Y | 0.75 | 10.40 | 9.43 |
| 51 | 7723-33-67 | 50 | 249 | 1060 | 0.00 | 2.00 | 1.00 | H-Y | 0.75 | 31.75 | 12.27 |
| 52 | 7723-33-68 | 51 | 249 | 1054 | 0.00 | 2.00 | 1.00 | H-Y | 0.75 | 32.77 | 12.34 |
| 53 | 7893-83-05 | 57 | 288 | 30 | 0.00 | 0.00 | 1.00 | 13% AL2O3/SIO2 | 0.18 | 27.87 | 2.30 |
| 54 | 7893-83-06 | 53 | 287 | 30 | 0.00 | 0.00 | 1.00 | 13% AL2O3/SIO2 | 0.18 | 25.08 | 2.34 |
| 55 | 7893-85-12 | 62 | 288 | 30 | 0.50 | 0.00 | 0.50 | 13% AL2O3/SIO2 | 0.18 | 15.53 | 2.63 |
| 56 | 7893-85-11 | 54 | 287 | 30 | 0.50 | 0.00 | 0.50 | 13% AL2O3/SIO2 | 0.18 | 17.16 | 2.63 |
| 57 | 7893-82-03 | 55 | 288 | 970 | 0.00 | 0.00 | 1.00 | 13% AL2O3/SIO2 | 0.18 | 52.45 | 3.64 |
| 58 | 7893-82-04 | 56 | 288 | 975 | 0.00 | 0.00 | 1.00 | 13% AL2O3/SIO2 | 0.18 | 50.67 | 3.83 |
| 63 | 7893-93-18 | 66 | 289 | 930 | 0.75 | 2.00 | 0.25 | 13% AL2O3/SIO2 | 1.10 | 33.83 | 8.28 |
| 64 | 7893-93-17 | 65 | 289 | 930 | 0.75 | 2.00 | 0.25 | 13% AL2O3/SIO2 | 1.10 | 32.45 | 8.44 |
| 65 | 7893-93-16 | 68 | 290 | 930 | 0.75 | 2.00 | 0.25 | 13% AL2O3/SIO2 | 2.20 | 18.73 | 9.12 |
| 66 | 7893-85-14 | 64 | 289 | 890 | 0.50 | 2.00 | 0.50 | 13% AL2O3/SIO2 | 1.17 | 28.99 | 9.17 |
| 67 | 7893-85-13 | 63 | 288 | 890 | 0.50 | 2.00 | 0.50 | 13% AL2O3/SIO2 | 1.17 | 26.69 | 9.26 |
| 68 | 7893-93-15 | 67 | 290 | 930 | 0.75 | 2.00 | 0.25 | 13% AL2O3/SIO2 | 2.20 | 16.97 | 13.39 |

TABLE 6
CONVERSION OF N-ISOPROPYLANILINE

| OBS | RUN | ANILINE MOLE PCT | N-IPA MOLE PCT | 2-IPA MOLE PCT | 4-IPA MOLE PCT | N,2-DIPA MOLE PCT | 2,4-DIPA MOLE PCT | 2,6-DIPA MOLE PCT | 2,4,6-TIPA MOLE PCT | CONV | O-P |
|---|---|---|---|---|---|---|---|---|---|---|---|
| 1 | 5 | 56.66 | 36.36 | 3.78 | 0.00 | 0.00 | 0.00 | 0.00 | 0.00 | 6.97 | >40 |
| 2 | 20 | 57.32 | 35.59 | 3.42 | 0.00 | 0.00 | 0.00 | 0.00 | 0.00 | 7.09 | >40 |
| 3 | 23 | 69.12 | 18.27 | 10.10 | 0.00 | 0.42 | 0.00 | 0.54 | 0.00 | 12.61 | >61 |
| 4 | 1 | 72.91 | 2.93 | 14.07 | 1.69 | 0.00 | 0.60 | 0.51 | 0.00 | 24.16 | 6.37 |
| 5 | 2 | 74.80 | 1.62 | 13.78 | 1.67 | 0.00 | 0.55 | 0.45 | 0.00 | 23.58 | 6.40 |
| 8 | 7 | 84.89 | 0.72 | 9.06 | 1.14 | 0.00 | 0.00 | 0.00 | 0.00 | 14.38 | 7.93 |
| 9 | 6 | 83.98 | 2.10 | 9.21 | 1.13 | 0.00 | 0.00 | 0.00 | 0.00 | 13.92 | 8.13 |
| 10 | 18 | 53.34 | 16.37 | 20.75 | 1.66 | 1.78 | 1.23 | 1.47 | 0.00 | 30.29 | 8.29 |
| 12 | 19 | 53.72 | 15.58 | 21.45 | 1.69 | 1.75 | 1.17 | 1.42 | 0.00 | 30.70 | 8.61 |
| 14 | 11 | 17.81 | 5.39 | 43.65 | 1.20 | 4.08 | 2.16 | 19.66 | 1.54 | 76.80 | 13.74 |
| 15 | 10 | 29.42 | 8.30 | 39.30 | 0.73 | 3.60 | 2.02 | 14.30 | 1.28 | 62.28 | 14.19 |
| 16 | 9 | 72.33 | 15.29 | 10.08 | 0.71 | 0.00 | 0.00 | 0.00 | 0.00 | 12.38 | 14.27 |
| 17 | 12 | 16.97 | 5.39 | 48.76 | 1.17 | 4.68 | 2.20 | 18.99 | 1.68 | 77.63 | 14.35 |
| 18 | 16 | 12.11 | 3.88 | 49.54 | 1.30 | 5.11 | 2.29 | 24.18 | 1.87 | 84.02 | 14.47 |
| 19 | 22 | 72.59 | 17.75 | 7.42 | 0.51 | 0.00 | 0.00 | 0.00 | 0.00 | 9.66 | 14.55 |
| 20 | 17 | 12.25 | 3.90 | 50.03 | 1.28 | 5.16 | 2.31 | 23.94 | 1.84 | 83.85 | 14.57 |
| 21 | 14 | 13.79 | 4.40 | 50.27 | 1.20 | 5.08 | 2.18 | 21.78 | 1.63 | 81.81 | 15.39 |
| 22 | 13 | 16.68 | 5.31 | 48.24 | 1.07 | 4.88 | 2.15 | 18.78 | 1.32 | 78.01 | 15.82 |
| 23 | 15 | 14.89 | 4.69 | 51.33 | 1.16 | 5.15 | 1.27 | 20.54 | 1.56 | 80.42 | 19.35 |
| 24 | 4 | 40.71 | 18.62 | 26.44 | 0.00 | 3.67 | 1.50 | 7.96 | 0.45 | 40.66 | 19.45 |
| 25 | 3 | 41.85 | 29.38 | 18.16 | 0.00 | 2.52 | 0.99 | 3.87 | 0.00 | 28.76 | 24.83 |
| 26 | 8 | 47.84 | 19.18 | 23.67 | 0.00 | 2.36 | 0.98 | 5.23 | 0.00 | 32.98 | 31.82 |
| 27 | 21 | 53.39 | 27.10 | 13.61 | 0.00 | 1.10 | 0.46 | 1.43 | 0.00 | 19.52 | 35.08 |
| 28 | 37 | 40.23 | 55.20 | 1.75 | 0.00 | 1.60 | 0.00 | 0.00 | 0.00 | 4.57 | >40 |

TABLE 6-continued

| | | | CONVERSION OF N-ISOPROPYLANILINE | | | | | | | |
|---|---|---|---|---|---|---|---|---|---|---|
| OBS | RUN | ANILINE MOLE PCT | N-IPA MOLE PCT | 2-IPA MOLE PCT | 4-IPA MOLE PCT | N,2-DIPA MOLE PCT | 2,4-DIPA MOLE PCT | 2,6-DIPA MOLE PCT | 2,4,6-TIPA MOLE PCT | CONV | O-P |
| 29 | 38 | 40.17 | 55.34 | 1.80 | 0.00 | 1.53 | 0.00 | 0.00 | 0.00 | 4.48 | >40 |
| 30 | 28 | 63.97 | 26.59 | 2.77 | 3.21 | 0.56 | 0.16 | 0.30 | 0.00 | 9.44 | 1.08 |
| 31 | 29 | 62.85 | 27.64 | 2.91 | 3.30 | 0.56 | 0.00 | 0.33 | 0.00 | 9.51 | 1.15 |
| 32 | 30 | 52.21 | 39.39 | 2.97 | 2.32 | 0.88 | 0.00 | 0.00 | 0.00 | 8.40 | 1.66 |
| 33 | 31 | 53.29 | 37.12 | 3.63 | 2.72 | 1.00 | 0.00 | 0.32 | 0.00 | 9.60 | 1.82 |
| 34 | 32 | 31.18 | 60.06 | 2.80 | 1.40 | 1.63 | 0.42 | 0.54 | 0.00 | 8.76 | 2.72 |
| 35 | 35 | 62.97 | 31.08 | 2.70 | 1.19 | 0.57 | 0.00 | 0.41 | 0.00 | 5.95 | 3.10 |
| 36 | 48 | 73.31 | 21.68 | 1.82 | 0.64 | 0.39 | 0.00 | 0.00 | 0.00 | 5.01 | 3.43 |
| 37 | 33 | 30.02 | 59.97 | 3.48 | 1.44 | 2.27 | 0.37 | 0.57 | 0.00 | 10.01 | 3.49 |
| 38 | 34 | 61.14 | 30.63 | 3.57 | 1.15 | 1.03 | 0.00 | 0.99 | 0.00 | 8.22 | 4.87 |
| 39 | 46 | 49.36 | 15.83 | 19.23 | 1.99 | 3.78 | 1.67 | 6.88 | 0.42 | 34.81 | 7.31 |
| 40 | 40 | 66.21 | 21.64 | 7.20 | 1.23 | 1.49 | 0.00 | 0.38 | 0.00 | 12.16 | 7.36 |
| 41 | 49 | 68.30 | 22.72 | 5.50 | 0.90 | 1.15 | 0.00 | 0.00 | 0.00 | 8.97 | 7.36 |
| 42 | 47 | 25.90 | 18.62 | 28.29 | 2.62 | 7.13 | 3.21 | 13.11 | 0.73 | 55.48 | 7.41 |
| 43 | 36 | 38.39 | 56.70 | 1.80 | 0.48 | 1.79 | 0.00 | 0.00 | 0.00 | 4.91 | 7.47 |
| 44 | 44 | 50.34 | 22.18 | 18.56 | 2.41 | 3.66 | 0.85 | 2.33 | 0.00 | 27.49 | 7.53 |
| 45 | 41 | 57.77 | 22.74 | 13.02 | 1.65 | 2.53 | 0.35 | 1.04 | 0.00 | 19.50 | 8.29 |
| 46 | 42 | 55.54 | 23.23 | 14.47 | 1.76 | 2.94 | 0.41 | 1.25 | 0.00 | 21.23 | 8.58 |
| 47 | 45 | 51.09 | 22.93 | 14.94 | 1.64 | 3.79 | 0.91 | 3.84 | 0.00 | 25.98 | 8.84 |
| 48 | 52 | 62.87 | 14.94 | 14.48 | 1.51 | 2.16 | 0.62 | 2.33 | 0.00 | 22.19 | 8.88 |
| 49 | 39 | 63.70 | 23.09 | 7.96 | 1.11 | 1.75 | 0.00 | 0.38 | 0.00 | 13.22 | 9.09 |
| 50 | 43 | 76.47 | 13.13 | 6.68 | 0.81 | 0.60 | 0.00 | 0.34 | 0.00 | 10.40 | 9.43 |
| 51 | 50 | 31.37 | 36.88 | 16.46 | 1.44 | 8.87 | 0.97 | 4.22 | 0.00 | 31.75 | 12.27 |
| 52 | 51 | 30.32 | 36.91 | 16.18 | 1.46 | 10.00 | 1.03 | 4.49 | 0.00 | 32.77 | 12.34 |
| 53 | 57 | 58.88 | 13.25 | 14.40 | 3.73 | 1.95 | 3.57 | 2.29 | 0.80 | 27.87 | 2.30 |
| 54 | 53 | 60.45 | 14.47 | 14.47 | 3.86 | 2.00 | 3.39 | 2.15 | 0.71 | 25.08 | 2.34 |
| 55 | 62 | 76.44 | 8.03 | 11.61 | 3.30 | 0.63 | 1.72 | 0.97 | 0.00 | 15.53 | 2.63 |
| 56 | 54 | 76.09 | 6.75 | 12.67 | 3.51 | 0.61 | 1.96 | 1.12 | 0.00 | 17.16 | 2.63 |
| 57 | 55 | 33.23 | 14.33 | 24.96 | 2.80 | 6.47 | 5.92 | 7.15 | 1.88 | 52.45 | 3.64 |
| 58 | 56 | 33.28 | 16.05 | 24.31 | 2.95 | 7.35 | 5.49 | 6.86 | 1.63 | 50.67 | 3.83 |
| 63 | 66 | 46.95 | 19.22 | 19.74 | 1.56 | 5.74 | 1.68 | 3.81 | 0.29 | 33.83 | 8.28 |
| 64 | 65 | 48.47 | 19.08 | 19.44 | 1.58 | 5.41 | 1.53 | 3.56 | 0.26 | 32.45 | 8.44 |
| 65 | 68 | 61.67 | 19.61 | 12.21 | 1.23 | 3.29 | 0.60 | 1.18 | 0.00 | 18.73 | 9.12 |
| 66 | 64 | 40.48 | 30.52 | 13.14 | 1.39 | 7.61 | 1.13 | 2.21 | 0.00 | 28.99 | 9.17 |
| 67 | 63 | 42.05 | 31.26 | 11.34 | 1.22 | 6.76 | 0.93 | 1.80 | 0.00 | 26.69 | 9.26 |
| 68 | 67 | 63.67 | 19.35 | 11.48 | 1.16 | 3.04 | 0.00 | 1.00 | 0.00 | 16.97 | 13.39 |

Review of the data Tables 1 and 3 show that addition of aromatic amine to N-alkylate at comparable pressure increases the relative amount of N-alkylate in the product stream; i.e., reduces conversion when reaction conditions are kept constant. The data suggest N-alkylation and ring alkylation are competing reactions. Thus, diluting N-alkylate with aniline, without adding olefin, will increase para-alkylation rather than decrease it at comparable conversion. Compare runs 35, 30, and 39 (OBS 37, 48, 45). The data suggest that appropriate steps can be taken to control the reaction of N-alkylates in terms of ortho-regioselectivity required in ring alkylation.

The data in Table 1 clearly illustrate the importance of maintaining a positive olefin molar ratio and not simply increasing the reaction pressure in the conversion of N-alkylate to ortho-alkylated product. This is particularly true in the case of the H-Y and silica-alumina catalyst which have a capability of producing higher levels of the para-isomer than does gamma-alumina. Gamma-alumina is rather unique in itself. Run 2 and Run 18 (OBS 3 and 14) illustrate, as a general rule, when one increases the pressure of the reaction without adding olefin, there is a tendency to produce only a slight increase in the ortho-para isomer ratio. These runs show that going from 30-960 psig with no olefin present, the ortho-para ratio went from about 6 to 8:1 and conversion increased from 23 to 34%. Also compare runs 28, 29, 30, and 31 (OBS 28, 29, 37 and 48). These runs show that when no olefin was present and at 40 psig the catalyst gave about 10% conversion with an ortho-para ratio of 1:1 (Runs 28 and 29) and about the same when the pressure was increased to about 1000 psig (OBS 37, 48). One can essentially double and triple the ortho-para ratio as compared to the previous runs under identical conditions by using a high positive pressure with the addition of olefin, e.g., 1000 psig of olefin with the olefin being present in a molar ratio of at least 2 moles olefin per mole of amine feedstock. Runs 28–33 and runs 4, 40, 42 and 43 are illustrative (OBS 28, 29, 30, 31, 49, 35, 32 and 34).

Tables 3 and 4, which are arranged in order of ascending conversion show that conversions in excess of 30% and at ortho to para isomer ratios in excess of 6:1 are obtained. When a high positive pressure of propylene is present, conversion and the ortho-para ratio increases dramatically. For example conversion can be increased from 30% to about 75% and the ortho-para ratio can be increased from 8 to about 15:1. Also note para-alkylation from N-isopropylaniline can be held to a minimum by the maintenance of a high olefin to aniline/N-isopropylaniline molar ratio (runs 25, 27, 17 and 16, (OBS 17, 18, 26 and 27) compared to runs 5 and 20 (OBS 1, 2).

The trends with respect to conversion and ortho-para ratio set forth with gamma-alumina holds true for both the H-Y and silica-alumina catalyst. As with gamma alumina, the H-Y and silica-alumina catalysts show conversion increases with high olefin pressure and the transalkylation to the para isomer is minimized thereby maintaining a high ortho-para ratio. (Runs 35, 34, 52, 44 and 50 are illustrative) (OBS 32, 33, 46, 48 and 49).

Tables 5 and 6 are arranged in ascending order of ortho to para ratio and highlight that feature of the invention by showing high ortho to para ratios can be obtained at high conversion. Many of the runs discussed with respect to Tables 1-4 become easy to isolate in reviewing the ortho to para sorting followed by a review of the corresponding conversion values.

The H-Y catalyst runs demonstrate the effect of LHSV on conversion of N-alkylates. It can be readily seen that the degree of conversion is dependent on residence time. Longer residence time, i.e., lower LHSV, brings about higher conversion of N-alkylates. Compare runs 51 and 36 (OBS 46 and 50).

What is claimed is:

1. In a process for forming ring alkylated aromatic amines by reacting an olefin with an aromatic amine in the presence of an acidic catalyst, the improvement for enhancing the conversion of a $C_{2-4}$ N-alkylated aniline to a ring alkylated aniline where the ratio of ortho-alkylated aniline to para-alkylated aniline product is greater than about 3 to 1 and the conversion of aromatic amine to ring alkylated aniline is greater than about 20% which comprises:

contacting a $C_{2-4}$ olefin with an aromatic feed containing N-alkylated aniline of the structure

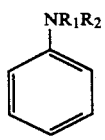

where, $R_1$ is $C_{2-4}$ alkyl and $R_2$ is hydrogen or $C_{2-4}$ alkyl;
maintaining an olefin to amine molar ratio of about 10-1:1;
maintaining a pressure of at least 50 psig in the reaction zone; and
utilizing a solid phase, acidic catalyst.

2. The process of claim 1 wherein the pressure in said reaction is at least 200 psig.

3. The process of claim 2 wherein reaction temperature is maintained sufficiently low within a temperature range of from 50° to 425° C. and wherein the space velocity is maintained sufficiently high at such temperature such that a significant amount of ortho-alkylated product produced in the reaction zone is not rearranged to the para isomer.

4. The process of claim 3 wherein the liquid hourly space velocity of the feed containing N-alkylated aniline to the reactor is from 0.05 to 4.0 hours$^{-1}$.

5. The process of claim 4 wherein the pressure in the reaction zone is maintained at level from about 200 to 2000 psig.

6. The process of claim 5 wherein the temperature utilized for converting N-alkylated aniline is from 200° to 425° C. when the olefin is ethylene, 100° to 375° C. when the olefin is propylene and the temperature is from 50° to 250° C. when the olefin is isobutylene.

7. The process of claim 6 wherein the solid phase, acidic catalyst is a hydrogen or rare earth exchanged zeolite and X is O.

8. The process of claim 6 wherein the catalyst is a silica-alumina having from about 5 to 25 percent alumina.

9. The process of claim 6 wherein said catalyst is gamma-alumina.

10. The process of claim 4 wherein said olefin is propylene.

11. A process for forming an isopropyl aniline where the isopropyl group is ortho to the amine which comprises reacting a feed containing an N-isopropyl aniline with propylene in the presence of gamma alumina, silica-alumina, or zeolite at a temperature from 100° to 375° C., a pressure from 200 to 2000 psig and a mole ratio of propylene to N-isopropyl aniline of from 10:1 to 1:1, and a space velocity of 0.05 to 4.0 hours$^{-1}$.

12. A process for preparing a ring alkylated product from an N-alkylated aniline wherein the ortho to para isomer ratio exceeds 6:1 and a conversion level greater than 30% by weight of incoming N-alkylated reactant which comprises contacting an aromatic amine feed containing at least 25 mole percent of an N-alkylated reactant of the formula where, $R_1$ is $C_{2-4}$ alkyl, and $R_2$ is hydrogen or $C_{2-4}$ alkyl with a $C_{2-4}$ olefin in the presence of gamma-alumina or an acidic zeolite catalyst, maintaining a temperature from 150° to 350° C., maintaining a mole ratio of olefin to N-alkylated reactant of from 2-10:1, and maintaining a pressure from 500 to 1000 psig and an LHSV of from 0.1 to 1 hr$^{-1}$.

13. The process of claim 12 wherein said olefin is propylene, said aromatic feed contains from 0 to 0.5 moles aniline and 0.5 to 1 mole of N-isopropyl aniline per mole of aromatic feed, said catalyst is a hydrogen or rare earth exchanged Y zeolite, the contacting is carried out a pressure from about 200 to about 2000 psig and the temperature is from 225°-275° C. and X is O.

14. The process of claim 13 wherein the ring alkylated product is withdrawn from the reactor when the rate of formation of the ortho-alkylated product is slower than rate of decomposition of said ortho-alkylated product.

* * * * *